(12) United States Patent
Tandon et al.

(10) Patent No.: US 11,591,561 B2
(45) Date of Patent: Feb. 28, 2023

(54) METHOD AND APPARATUS FOR ELECTROPORATION OF ACOUSTICALLY-ALIGNED CELLS

(71) Applicant: The Charles Stark Draper Laboratory, Inc., Cambridge, MA (US)

(72) Inventors: Vishal Tandon, Roxbury Crossing, MA (US); Charles A. Lissandrello, Newtonville, MA (US); Ryan A. Dubay, Cambridge, MA (US); Rebecca Christianson, Cambridge, MA (US); Jenna Leigh Balestrini, Boston, MA (US); Peter Hsi, Waltham, MA (US); Jason Fiering, Boston, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 982 days.

(21) Appl. No.: 16/168,464

(22) Filed: Oct. 23, 2018

(65) Prior Publication Data

US 2019/0119624 A1 Apr. 25, 2019

Related U.S. Application Data

(60) Provisional application No. 62/575,669, filed on Oct. 23, 2017.

(51) Int. Cl.
*C12M 1/42* (2006.01)
*A61K 9/00* (2006.01)
(Continued)

(52) U.S. Cl.
CPC ........... *C12M 35/02* (2013.01); *A61K 9/0009* (2013.01); *A61N 1/327* (2013.01);
(Continued)

(58) Field of Classification Search
CPC ........... A61K 9/0009; B01L 2200/0647; B01L 2300/0645; B01L 2400/0436;
(Continued)

(56) References Cited

U.S. PATENT DOCUMENTS

| | | | | |
|---|---|---|---|---|
| 2002/0137121 A1* | 9/2002 | Rubinsky | ........... | G01N 33/5014 435/29 |
| 2013/0292582 A1* | 11/2013 | Kaduchak | ............ | G01N 29/222 250/459.1 |
| 2016/0108433 A1* | 4/2016 | Fair | ........................ | C12N 15/87 435/173.6 |

FOREIGN PATENT DOCUMENTS

WO WO 2015047502 4/2015
WO WO 2018022158 2/2018

OTHER PUBLICATIONS

Adamo, A., et al., "Flow-through comb electroporation device for delivery of macromolecules," Anal. Chem., 85: 1637-1641 (2013).
(Continued)

*Primary Examiner* — David W Berke-Schlessel
*Assistant Examiner* — Trent R Clarke
(74) *Attorney, Agent, or Firm* — HoustonHogle LLP (57) ABSTRACT

Transfer of genetic and other materials to cells is conducted in a hands-free, automated and continuous process that includes flowing the cells between electroporation electrodes to facilitate delivery of a payload into the cells, while acoustophoretically focusing the cells. Also described is a control method for the acoustophoretic focusing of cells that includes detecting locations of cells flowing through a channel, such as with an image analytics system, and modulating a drive signal to an acoustic transducer to change the locations of the cells flowing in the channel. Finally, an electroporation driver module is described that uses a digital to analog converter for generating an electroporation waveform and an amplifier for amplifying the
(Continued)

electroporation waveform for application to electroporation electrodes.

12 Claims, 8 Drawing Sheets

(51) Int. Cl.
  *C12N 15/87* (2006.01)
  *C12M 3/06* (2006.01)
  *B01L 3/00* (2006.01)
  *A61N 1/32* (2006.01)
  *B82Y 5/00* (2011.01)
  *A61N 7/00* (2006.01)

(52) U.S. Cl.
  CPC ..... *B01L 3/50273* (2013.01); *B01L 3/502715* (2013.01); *B01L 3/502761* (2013.01); *C12M 23/16* (2013.01); *C12M 35/04* (2013.01); *C12N 15/87* (2013.01); *A61N 7/00* (2013.01); *B01L 2200/0647* (2013.01); *B01L 2300/0645* (2013.01); *B01L 2300/0654* (2013.01); *B01L 2300/0816* (2013.01); *B01L 2400/0436* (2013.01); *B82Y 5/00* (2013.01)

(58) Field of Classification Search
  CPC ........... B01L 3/502715; B01L 3/50273; B01L 3/502761; B01L 2300/0654; B82Y 5/00; C12M 35/02; C12M 35/04; C12M 23/16; C12N 15/87
  See application file for complete search history.

(56) References Cited

OTHER PUBLICATIONS

Chang, L., et al., "Dielectrophoresis-assisted 3D nanoelectroporation for non-viral cell transfection in adoptive immunotherapy," Lab Chip, 15: 3147-3153 (2015).

Chang, L., et al., "Micro-/Nano-scale Electroporation," Lab Chip, 16: 4047-4062 (2016).

Geng, T., et al., "Microfluidic electroporation for cellular analysis and delivery," Lab Chip., 13: 3803-3821 (2013).

Kotnik, T., et al., "Analytical Description of Transmembrane Voltage Induced by Electric Fields on Spheroidal Cells," Biophysical Journal, 79(2): 670-679 (2000).

Lissandrello, C., et al., "Purification of Lymphocytes by Acoustic Separation in Plastic Microchannels," SLAS Technology, 23(4): 352-363 (2018).

Longsine-Parker, W., et al., "Microfluidic Electro-Sonoporation: A Multi-Modal Cell Poration Methodology Through Simulataneous Application of Electric Field and Ultrasonic Wave," Lab Chip, 13 (11): 2144-2152 (2013).

Mueller, A., et al., "Continuous Acoustic Separation i na Thermoplastic Microchannel," J. Micromech. Microeng., 23: 1-10 (2013).

Partial International Search, dated Jan. 28, 2019, from International Application No. PCT/US2018/057101, filed on Oct. 23, 2018. 10 pages.

Vickers, D.A.L., et al., "Direct drug cocktail analyses using microscale vortex-assisted electroporation," Anal. Chem., 86:10099-10105 (2014).

Voldman, J., "Electrical Forces for Microscale Cell Manipulation," Annu. Rev. Biomed. Eng., 8(1): 425-454 (2006).

Wang, J., et al., "Vortex-assisted DNA delivery," Lab Chip, 10 (16): 2057-2061 (2010).

Yun, H., et al., "Sequential multi-molecule delivery using vortex-assisted electroporation," Lab Chip, 13:2764-2772 (2013).

Zhu, T., et al., "Electroporation based on hydrodynamic focusing of microfluidics with low dc voltage," Biomed. Microdevices, 12: 35-40 (2010).

International Preliminary Report on Patentability, dated May 7, 2020, from International Application No. PCT/US2018/057101, filed on Oct. 23, 2018. 9 pages.

International Search Report and Written Opinion, dated Apr. 9, 2019, from International Application No. PCT/US2018/057101, filed on Oct. 23, 2018. 17 pages.

\* cited by examiner

METHOD AND APPARATUS FOR ELECTROPORATION OF ACOUSTICALLY-ALIGNED CELLS

RELATED APPLICATIONS

This application claims the benefit under 35 USC 119(e) of U.S. Provisional Application No. 62/575,669, filed on Oct. 23, 2017, which is incorporated herein by reference in its entirety.

BACKGROUND OF THE INVENTION

Many applications in biology, medicine, pharmaceutical research and other areas use techniques in which "cargo," such as genetic materials, is introduced or delivered into cells. The term "transformation" is often used when working with bacteria or non-animal eukaryotic cells, including plant cells. "Transfection" almost always refers to work on eukaryotic cells, while "transduction" typically applies to virus-mediated gene transfer into eukaryotic cells. Cargoes of interest include not only DNA, siRNA, mRNA, RNP complexes, but also small molecules or proteins such as antibodies.

Existing delivery techniques employ a range of different modalities. Viral vectors can be used to deliver genes into cells. There are also mechanical methods such as microprecipitation, microinjection, liposomes, particle bombardment, sonoporation, laser-induced poration, bead transfection, gene guns, and magnetotransfection. Another technique relies on passing cells through narrow constrictions that cause cellular deformation.

Another common delivery technique is electroporation. Transient pores or "holes" are opened in the cell membrane to enable the transfer of the cargo into the cells. The creation of these holes allows the cargo's uptake, and thus altering, such as genetically modifying, the cells. Parameters considered when developing electroporation procedures include cell properties (cell size, shape, membrane structure, surface charge, for example), the cell environment, and attributes of the applied electric field, (e.g., pulse intensity, number of pulses, pulse duration, pulse shape and/or frequency). It is generally believed that membrane permeabilization during electroporation occurs after the applied electric field induces a threshold value in the transmembrane potential or "electroporation threshold" and that, at a given applied electric field, there is a threshold for the number of pulses and pulse length, needed for successful electroporation. The Schwan equation and related derivations are often used to estimate a cell's transmembrane potential that develops in response to relevant experimental parameters including applied field, cell size, conductivities of media, cellular cytosol, and cell membrane, and membrane thickness ("Analytical Description of Transmembrane Voltage Induced by Electric Fields on Spheroidal Cells", Biophysical Journal, Volume 79 August 2000 670-679).

Existing electroporation methods run the gamut. Examples include flow electroporation in which the cells are flowed through a region within the electroporation field, pulse-controlled electroporation and microfluidic devices with varying geometries (see L. Chang, L. Li, J. Shi, Y. Sheng, W. Lu, D. Gallego-Perez, L. J. Lee, Micro-/Nanoscale Electroporation, Lab Chip. (2016) 4047-4062, doi: 10.1039/C6LC00840B and T. Geng, C. Lu, Microfluidic electroporation for cellular analysis and delivery, Lab Chip. 13 (2013) 3803-21. doi:10.1039/c3lc50566a.), comb electroporation (see A. Adamo, A. Arione, A. Sharei, K. F. Jensen. Flow-through comb electroporation device for delivery of macromolecules, Anal. Chem. 85 (2013) 1637-1641. doi:10.1021/ac302887a.), DEP-assisted electroporation (see L. Chang, D. Gallego-Perez, X. Zhao, P. Bertani, Z. Yang, C.-L. Chiang, V. Malkoc, J. Shi, C. K. Sen, L. Odonnell, J. Yu, W. Lu, L. J. Lee, Dielectrophoresis-assisted 3D nanoelectroporation for non-viral cell transfection in adoptive immunotherapy, Lab Chip. 15 (2015) 3147-3153. doi: 10.1039/c51c00553a.), and electroporation in a hydrodynamically focused stream (T. Zhu, C. Luo, J. Huang, C. Xiong, Q. Ouyang, J. Fang, Electroporation based on hydrodynamic focusing of microfluidics with low de voltage, Biomed. Microdevices. 12 (2010) 35-40. doi:10.1007/s10544-009-9355-z.). Vortex-assisted electroporation that takes advantage of inertial focusing (J. Wang, Y. Zhan, V. M. Ugaz, C. Lu, Vortex-assisted DNA delivery, Lab Chip. 10 (2010) 2057. doi:10.1039/c004472e; H. Yun, S. C. Hur, Sequential multi-molecule delivery using vortex-assisted electroporation, Lab Chip. 13 (2013) 2764. doi:10.1039/c31c50196e; D. A. L. Vickers, M. Ouyang, C. H. Choi, S. C. Hur, Direct drug cocktail analyses using microscale vortex-assisted electroporation, Anal. Chem. 86 (2014) 10099-10105. doi:10.1021/ac501479g.) has been demonstrated.

SUMMARY OF THE INVENTION

Traditionally, the genetic modification of cells by electroporation has been conducted as a bulk, batch process using cuvettes. Less prevalent, commercial devices that might employ a flow configuration lack some automated features.

For instance, existing electroporation processes often utilize specialized, low-conductivity buffers that can negatively impact cell viability, especially with prolonged exposure. Batch processing, therefore, requires several buffer exchanges and wash steps, that render the approach touchlabor intensive, and difficult to scale up to meet growing large-batch manufacturing needs. Manual wash and/or filtration steps are also slow, so cells are still exposed to electroporation buffer for time scales on the order of minutes up to about an hour. These steps often are associated with cell loss (low cell recovery). Absent too is a high throughput of transfection.

In addition, some commercially available electroporation devices expose biologics to direct contact with electrodes, resulting in potential damage due to local heating and Faradaic by-products (hydronium ions, hydroxyl ions, chlorine, free radicals, and electrode breakdown by-products (e.g. aluminum ions and particulate)). Without fluid flow, many traditional electroporation approaches cannot transport heat away from thermally susceptible biological entities or cannot do this efficiently. In some cases, there is a lack of co-localization of cells (or other substrates) and payload (cargo), leading to inefficiencies and losses of (valuable) materials.

Other approaches use filter membranes embedded in microchannels and transmembrane pressure to align cells between electrodes. These systems require the cells to physically contact surfaces in the devices, which can result in strong non-specific adhesion, thus limiting recovery.

A need exists, therefore, for equipment and procedures that address at least some of the problems discussed above.

The present method and device aim to improve transfection efficiency, decrease processing time, and maintain high viability/integrity of the cells. The device uses the acoustic radiation force generated by one or more ultrasonic transducers to position cells along a predetermined line, such as a central streamline of flow, between a pair of electroporation electrodes. This acoustically-mediated migration enables precise control of cell or vesicle positioning in the electric field.

In contrast, in bulk electroporation systems, cell clumping and uncontrolled positioning with respect to the electrodes can lead to poorly-controlled exposure of cells to the electric field or uncontrolled vector integration.

Furthermore, the present system and method can operate at lower applied electroporation voltages. This enables construction of safer, lower-cost electronics for generating electric-field waveforms. In general, it is much more challenging to generate arbitrary waveforms at high voltage (~1000 V) than it is at low voltage (<~200 V). Operation at lower voltage increases the accessible parameter space for waveform generation.

The acoustic focusing employed manipulates and controls cell position between electrodes. At the same time, gas bubbles that form as a result of electrochemical reactions are pushed away from cells by a combination of fluid flow and acoustics.

In general, acoustic manipulation of cells for electroporation has four key advantages: (i) precise positioning of cells between electrodes in a single-file manner, allowing for more uniform exposure in an applied field; (ii) acoustophoretic manipulation can be carried out without exposing cells to high shear stresses; (iii) acoustophoretic positioning does not require cells to contact any surfaces, limiting non-specific adhesion and loss of cells; (iv) acoustic waves can push gas bubbles away from cells, enabling the use of electrochemical reactions to pass current through the fluid; (v) acoustophoretic-assisted electroporation allows for continuous processing, and (vi) acoustophoretic-assisted electroporation allows for in-line enrichment of select cells followed by immediate electroporation.

In general, according to one aspect, the invention features a method for introducing a payload into cells. The method comprises flowing the cells between electroporation electrodes to facilitate delivery of the payload into the cells, while acoustophoretically focusing the cells.

Preferably, flowing the cells comprises flowing the cells through a microchannel system that has a main channel ending in a trifurcating outlet in which the cells are directed to a cell output channel that couples with a center of the main channel.

Also preferably, the acoustophoretically focusing of the cells comprises driving an acoustic transducer that is attached to a substrate holding the electroporation electrodes.

The electroporation electrodes can be driven with an arbitrary waveform generator. In addition, the presence of cells can be sensed such as with sense electrodes located upstream of the electroporation electrodes. As part of a control scheme, the electroporation electrodes can be energized in response to sensing the presence of cells.

In general, according to another aspect, the invention features a device for introducing a payload into cells. The device comprises a microchannel system for flowing the cells between electroporation electrodes to facilitate delivery of the payload into the cells and an acoustic transducer for focusing the cells between the electroporation electrodes.

Preferably, the microchannel system includes a substrate having a main channel ending in a trifurcating outlet in which the cells are directed to a cell output channel that couples with a center of the main channel. The acoustic transducer is attached to the substrate, such as to its top or bottom.

The device can have two or more channels for receiving spent cargo/solution downstream of the electroporation electrodes. An arbitrary waveform generator can be used for driving the electroporation electrodes. Sense electrodes and a sensing module can further be provided detecting the presence of cells in the microchannel system.

In general, according to another aspect, the invention features a control method for acoustophoretic focusing of cells. The method comprises detecting locations of cells flowing through a channel and modulating a drive signal to an acoustic transducer to change the locations of the cells flowing in the channel.

The locations of the cells can be detected by capturing images of the cells in the channel and analyzing the images to determine the locations of the cells.

In general, according to another aspect, the invention features a device for processing cells. This device includes an image capture device for capturing images of cells flowing through a channel, an acoustic transducer for acoustophoretic focusing the cells in the channel, and a controller for modulating a drive signal to the acoustic transducer to change the locations of the cells flowing in the channel based on the captured images.

In general, according to another aspect, the invention features an electroporation driver module. The module comprises a digital to analog converter for generating an electroporation waveform and an amplifier for amplifying the electroporation waveform for application to electroporation electrodes.

In general, according to another aspect, the invention features an electroporation driver module. The module comprises a first analog to digital converter for detecting a voltage applied to electroporation electrodes and a second analog to digital converter for detecting a current flowing between the electroporation electrodes.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "and/or" includes any and all combinations of one or more of the associated listed items. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The invention generally relates to approaches for transferring one or more material(s) or agent(s), referred to herein as "cargo" or "payload", into or out of cells. In many cases, the cells are eukaryotic cells, typically having a diameter within the range of from about 5 to about 100 microns ($\mu$m). Cargo also can be transferred to or from other membrane bound structures, such as, for instance, liposomes, exosomes, micelles, etc.

Examples of cargo materials include but are not limited to small molecules, chromosomes, DNA, RNA, (e.g., mRNA, siRNA, gRNA, ssRNA), other genetic materials, oligomers, biomarkers, proteins, transposons, biomolecule complexes, small molecules, therapeutic agents, and so forth.

Figure 1:
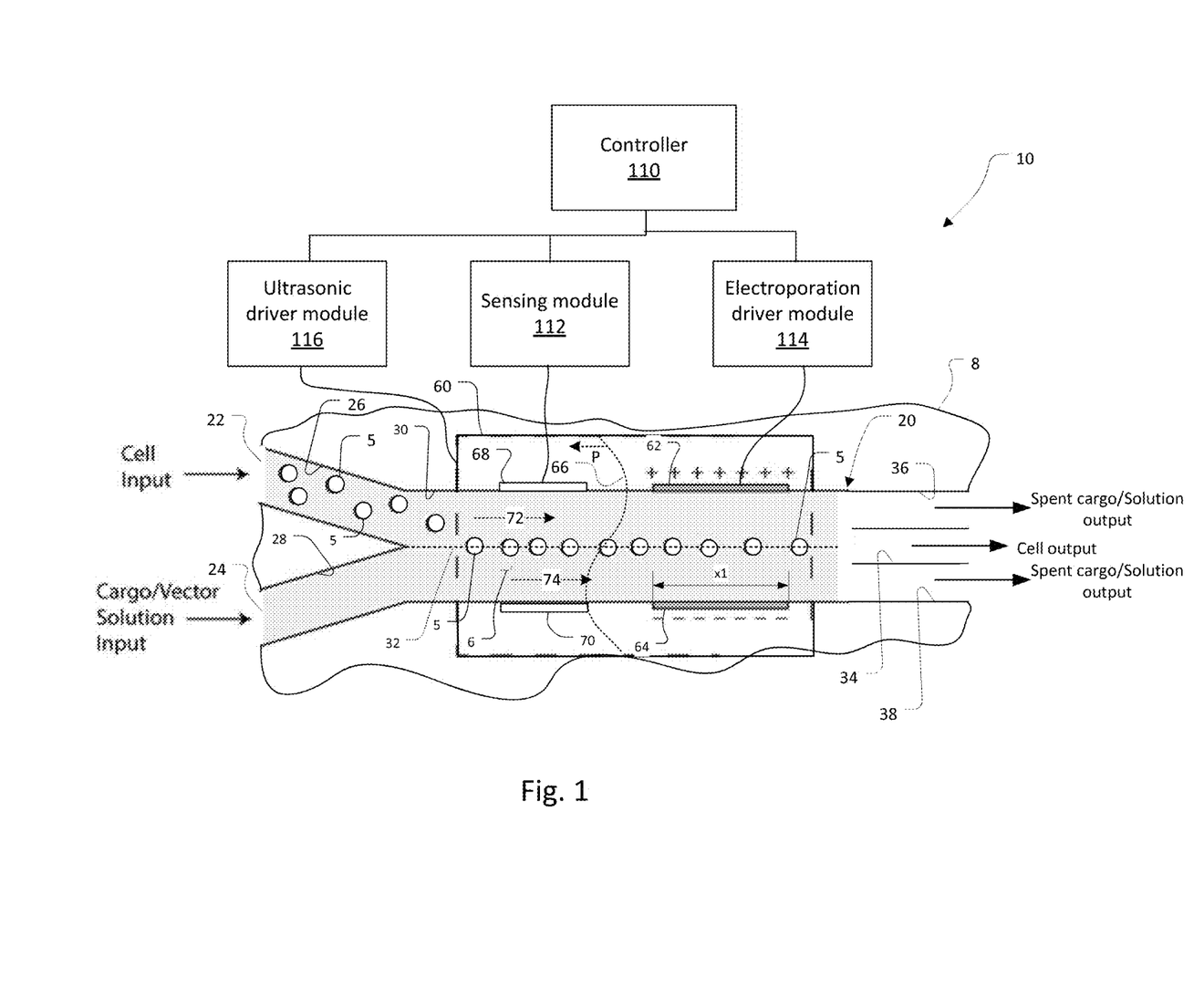
FIG. 1 is a schematic top plan view depicting a device for acoustophoretic focusing of cells for electroporation according to the invention.

FIG. 1 shows a device 10 employing acoustophoretic focusing of cells for electroporation, which has been constructed according to the principles of the present invention.

The device 10 comprises a microchannel system 20. This system 20 can be constructed from tubing or by fabricating or otherwise forming channels and ports in a typically rigid substrate 8. Preferably, the substrate 8 is a hard polymer substrate, such as cyclic olefin copolymer (COC) thermoplastic, a polyimide film, such as Kapton® film, polystyrene, PEI (polyetherimide), e.g., Ultem®, or a combination of various polymers or other hard substrates such as silicon, glass, and quartz or hybrid combinations of these materials. The substrate must be biocompatible and minimize absorption of chemical reagents and/or biological compounds. The substrate must also be compatible with at least one common sterilization technique, such as autoclave, ethylene oxide, or gamma irradiation.

The ports and channels in the microchannel system are preferably rectangular in cross section with the longer side of the ports and channels being in the plane of the figure and of the substrate 8. The ports and channels have width and height dimensions that range from 100 micrometers ($\mu$m) to 1000 $\mu$m. The length of the channels typically ranges from 5 millimeters (mm) to 30 mm.

In one embodiment, the microchannel system 20 has two or more inlet ports: a cell input port 22 and a solution and cargo input port 24. These ports 22, 24, provide access to a respective cell channel 26 and solution/cargo channel 28. The cell channel 26 and solution/cargo channel 28 merge with each other moving along the longitudinal direction of the microchannel system 20 into a main channel 30.

The main channel 30 ends in a trifurcating outlet. Specifically, in the illustrated embodiment, a cell output channel 34 couples in proximity to a center line 32 of the main channel. Two lateral spent cargo/solution channels 36, 38 couple along respective lateral sides of the main channel 30.

Cells and any incubation solution in the cell channel 26 and solution, such as electroporation solution, and the cargo in the cargo channel 28 typically have a flow rate Q in the range 1 microliters/minute ($\mu$l/min)<Q<1000 $\mu$l/min.

An acoustic radiation force is generated by a piezo electric acoustic transducer 60, for example. In the illustrated example, the acoustic transducer 60 is bonded to a bottom or top face of the substrate 8, under or over the main channel 30.

Under the influence of the acoustic radiation applied to the substrate 8 by the acoustic transducer 60, the cells are focused toward the central line 32 of the flow in the main channel 30 and leave the device through the central, cell output channel 34.

The side spent cargo/solution channels 36, 38 carry the spent cargo and solution along with gaseous electrochemical reaction products out of the microchannel system. Non-integrated cargo flows out of all three output channels 34, 36, 38.

A pair of electroporation electrodes 62, 64 is positioned in the region between the inlet and outlet of the main channel 30; for example, halfway along the length of the main channel 30. The electrodes 62, 64 are located on either lateral side of the main channel 30 and project into the main channel 30 in order to make electrical contact with the fluid in the main channel.

The electroporation electrodes 62, 64 may be patterned metallizations and fabricated on the substrate 8 using photolithographic processes. In other cases, the electrodes can simply be wires that are bonded to the substrate 8. The electroporation electrodes 62, 64 can be patterned onto the floor and ceiling of the main channel 30, or onto the sidewalls of the channel 30, in different examples.

The area of and especially the longitudinal length of the electroporation electrodes 62, 64 and flow rate of the fluid in the main channel 30 determine the residence time of cells in the electric/electroporation field. In general, the longitudinal length×1 of the electroporation electrodes 62, 64 can be between 100 μm-30 mm in length. The electrodes will typically be 100 μm to 1 mm in length in the case of wire electrodes. In the case of patterned planar electrodes, the length will typically be 1 mm and 30 mm. In addition, the electrodes may be flush with the walls of the main channel 30 or may extend into the fluid stream by as much as 200 μm. Chosen residence times can often vary from 100 microseconds (μs) to about a second.

The electroporation electrodes 62, 64 are energized by an electroporation drive module 114. It uses a controller 110 to instruct a DAQ 152 to generate arbitrary waveform signals that are then amplified for output by an amplifier box 160. A direct current (DC) or an alternative current (AC) can be applied across the electrodes 62, 64. In examples, the electroporation drive module 114 generates sinusoidal or pulse trains with periods/pulse widths ranging from 10 nanoseconds to 100's of microseconds. In other examples, the electroporation driver module 114 generates a DC current between the electrodes and across the main channel 30 and concomitant electric field. The current remains active while cells 5 flow through the device 10. The cells are of course shown exaggerated in size, for clarity. In general, the magnitude of the field is tuned for the specific cell type to be sufficient to achieve permeabilization, and is typically in the range of 2-200 kilovolts/meter (kV/m). The electroporation drive module 114 uses a voltage divider 156 and sense resistor 158 to measure the actual voltage and current delivered, respectively. Examples of measured current waveforms generated by the electroporation drive module 114 are shown in FIG. 6.

Alternatively, the electrical connection between the electroporation drive module and the fluid can be made at a location that is more remote from the cells, such as at open ports that are fluidically connected to the main channel. For example, fluidic connections from open ports to the main channel 30 can be made, and wire electrodes can be placed in the ports for connection to the electroporation drive module (such a configuration requires Faradaic current to pass through the electrodes). This would further reduce exposure of the cells to Faradaic by-products but would require the application of higher voltage.

The piezoelectric transducer 60 is driven by an ultrasonic drive module 116. In one mode of operation, the ultrasonic drive module 116 energizes the piezoelectric transducer 60 with a sinusoidally varying drive voltage, typically in the range of 400 to 1000 kHz. The drive voltage frequency is chosen such that a stable standing pressure wave 66 is generated laterally across the width of the main channel 30, i.e., transverse to the fluid flow direction.

Line 66 represents the standing pressure wave that is induced in the substrate 8 and the fluid 6 in the main channel 30 by the operation of the piezo electric acoustic transducer 60. For the fundamental focusing mode there is a single pressure node in the fluid with antinodes outside the main channel 30. This pressure gradient results in the migration of the more dense cells toward the centerline 32 of the cross-section of the main channel 30, and the migration of less-dense bubbles toward the channel's side walls. Cells then pass through the electrodes on their way to the outlet. Their exposure time to the electric field is controlled by the input flow rate.

Multiple exposures can be introduced with additional pairs of electroporation electrodes in sequence down the length of the main channel 30, in other embodiments.

The electric field generated between the electroporation electrodes 62, 64 and any additional electroporation electrodes makes the cells 5 temporarily permeable, and cargo thus enters the cells. Additional exposures may also permeabilize the nuclear membrane of the cell, enabling the transport of cargo to the nucleus.

In some embodiments, a pair of sensor electrodes 68, 70 is placed upstream of the electroporation electrodes 62, 64. Sensing module 112 applies a low-level AC voltage to the sensor electrodes 68, 70 and monitors the resulting current. In general, the current passing between the sensor electrodes 68, 70 is reduced in magnitude as cells pass through the region of the main channel between the sensor electrodes 68, 70. The current level is also generally proportional to the size of the cells 5. This current level is detected by the sensing module 112 and reported to the controller 110. The sensor information is used by the controller 110 for feedback control of the electroporation electrodes 62, 64, which are downstream.

In general, the controller 110 signals the electroporation driver module 114 to apply larger and smaller fields between the electroporation electrodes 62, 64. In one embodiment, the controller 110 uses larger fields for smaller cells and smaller fields for larger cells.

In other embodiments, the sensing module 112 also functions as a capacitive sensor. In this way, it detects the capacitance between the sensing electrodes 68 and 70. Generally, the capacitance between the electrodes will increase when the cells 5 are centered on and forming a line down the centerline 32 of the main channel 30. This capacitance information is reported to the controller 110, which then activates the electroporation driver module 114 based on whether the cells 5 are centered along the centerline 32.

Moreover, the controller 110 also preferably tunes the ultrasonic driver module 116 to center the cells, properly along the centerline 32 of the main channel 30. In general, the controller 110 controls the ultrasonic driver module 116 to change both the frequency of the drive signal applied to the acoustic transducer 60 and the magnitude of the drive signal, in order to ensure that the cells 5 are centered along the centerline 32 and preferably forming a single line of cells.

In some embodiments, multiple inlets such as the two, as illustrated, or three or more merge into the main acoustophoretic channel 30 to establish flows with 2 or 3 parallel sheath streams 72, 74 that create a laminar flow. These configurations allow the cargo to be introduced in a stream that is separate from that with the cells, affording additional control over the amount of cargo that is introduced into the cells.

The sheath streams 72, 74 may also be of a different immiscible phase (like an oil), where the cells would remain in an aqueous phase. This feature would allow for dielectric separation of the electrodes from the stream with the cells, enabling different electrical paradigms. Combined with acoustic focusing, this enables independent control over the positioning of cells (manipulated by the acoustic field, flow, and sensitive to electrical manipulation) and cargo (manipulated hydrodynamically and electrically, but indifferent to the acoustic field).

In some embodiments, acoustophoretic channels separate living cells from debris or dead and dying cells prior to the electroporation event.

Additionally, the acoustic radiation force is used to sort cells along different streamlines across the width of the channel based on their size, density, phenotype or compressibility, in some examples.

In another embodiment, cell or miscible separation is achieved using antibody labeling to distinguish cells or vesicles. The streamlines are then separated into multiple smaller channels or bins. Each channel may contain a set of electrodes to deliver a prescribed field to each subset of cells.

Figure 2A:
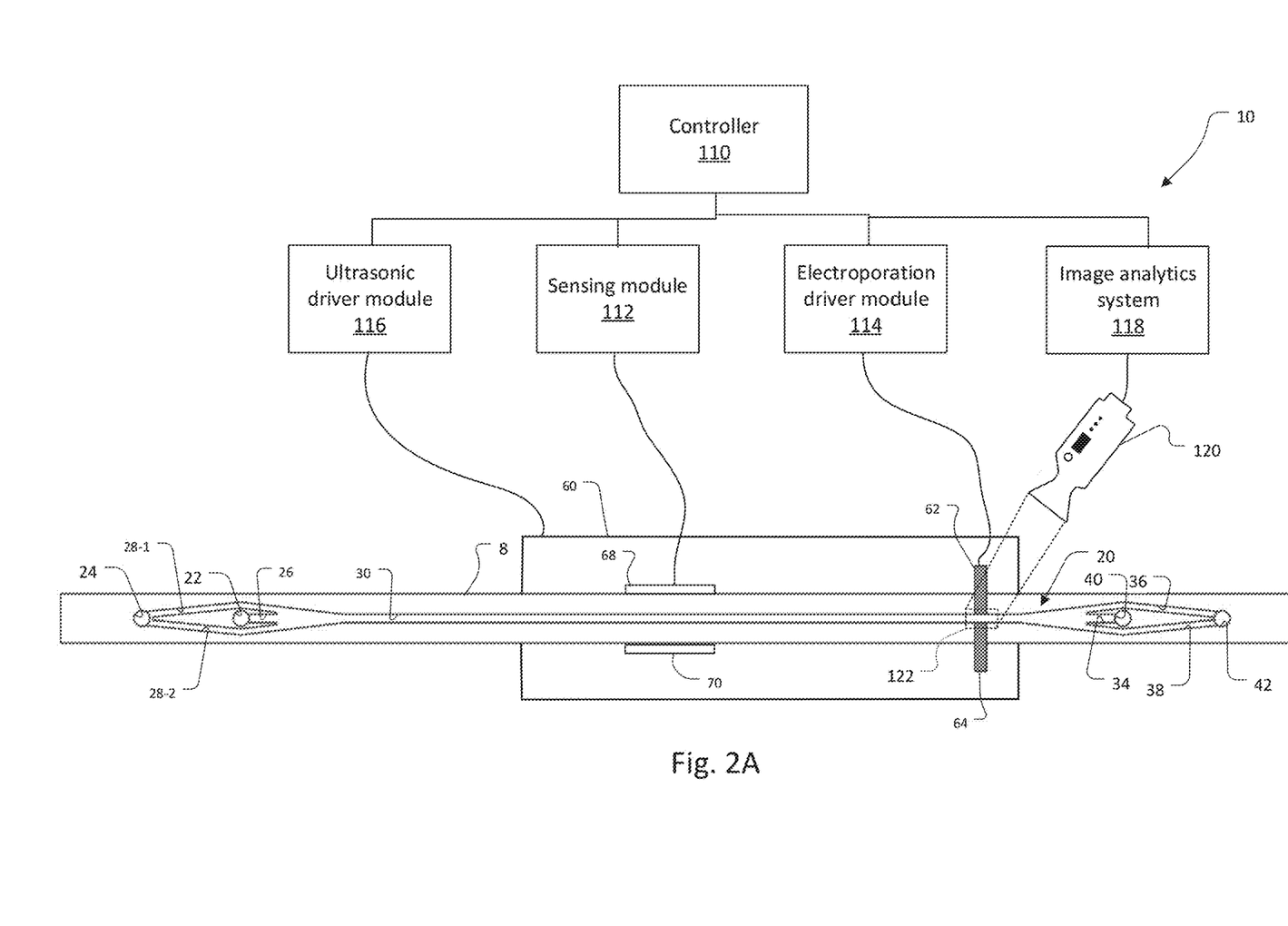
FIG. 2A is a schematic top plan view depicting a device for acoustophoretic focusing of cells for electroporation according to another embodiment.
Figure 2B:
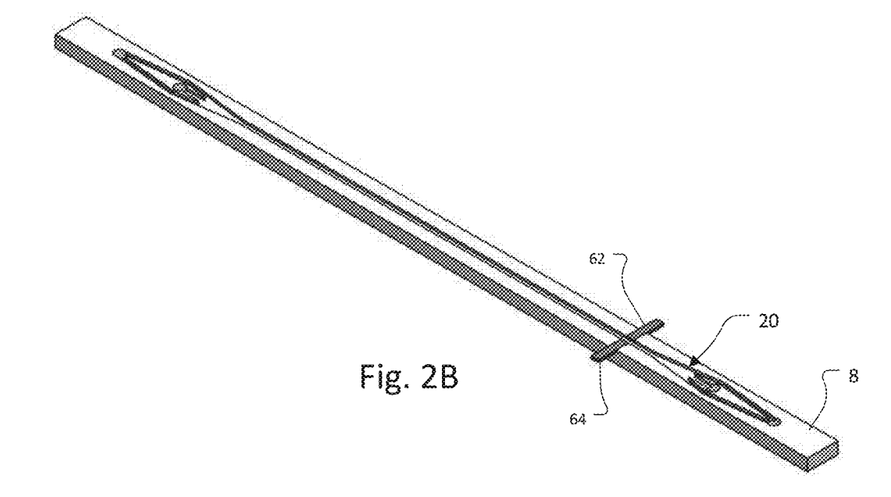
FIG. 2B is a perspective view of the substrate with the microchannel system.

FIG. 2A shows another embodiment of the device 10, which has also been constructed according to the principles of the present invention. Related FIG. 2B shows the substrate 8 and its microchannel system 20 in perspective.

The device 10 comprises the microchannel system 20 fabricated by forming channels in the rigid substrate 8, which is preferably a hard polymer substrate or otherwise, as described earlier.

This microchannel system 20 has two inlet ports. The cell input port 22 typically receives a tube carrying the cells in the incubation solution. Similarly, the solution and cargo input port 24 receives the cargo in its solution. These ports 22, 24 provide access to the cell channel 26 and two solution/cargo channels 28-1, 28-2, respectively. The two solution/cargo channels 28-1, 28-2 branch away from each other and then re-converge along the longitudinal direction. The cell channel 26 and the two solution/cargo channels 28-1, 28-2 then merge with each other moving along the longitudinal direction into a main channel 30.

The main channel 30 ends in a trifurcating outlet. The cell output channel 34 couples in proximity to the center line of the main channel 30. The two lateral spent cargo/solution channels 36, 38 couple along respective lateral sides of the main channel 30.

The cell output channel 34 couples to a cell output port 40. On the other hand, the spent cargo/solution channels 36, 38 diverge and then converge at a spent solution output port 42.

The piezo electric acoustic transducer 60 is bonded to a bottom or top face of the substrate 8, under the main channel 30.

Here, the pair of electroporation electrodes 62, 64 is positioned near the end of the main channel 30. The electrodes 62, 64 are located on either lateral side of the main channel and project into the main channel 30 in order to make electrical contact with the fluid in the main channel. Here, the electrodes might be platinum wires bonded to the substrate 8.

Moreover, the controller 110 also preferably uses a feedback control loop to tune the ultrasonic driver module 116 based on whether the cells are properly centered along the centerline 32 of the main channel 30.

In this embodiment, a microscope video image capture device 120 captures magnified images of the fluid in the main channel 30 in the inter-electrode region 122 between the two opposed ends 62-E, 64-E of the two electroporation electrodes 62, 64. Typically, the microscope video image capture device 120 captures images magnified at greater than 100× so that the cells and possibly dyed cells or other media are visible.

Figure 3A:
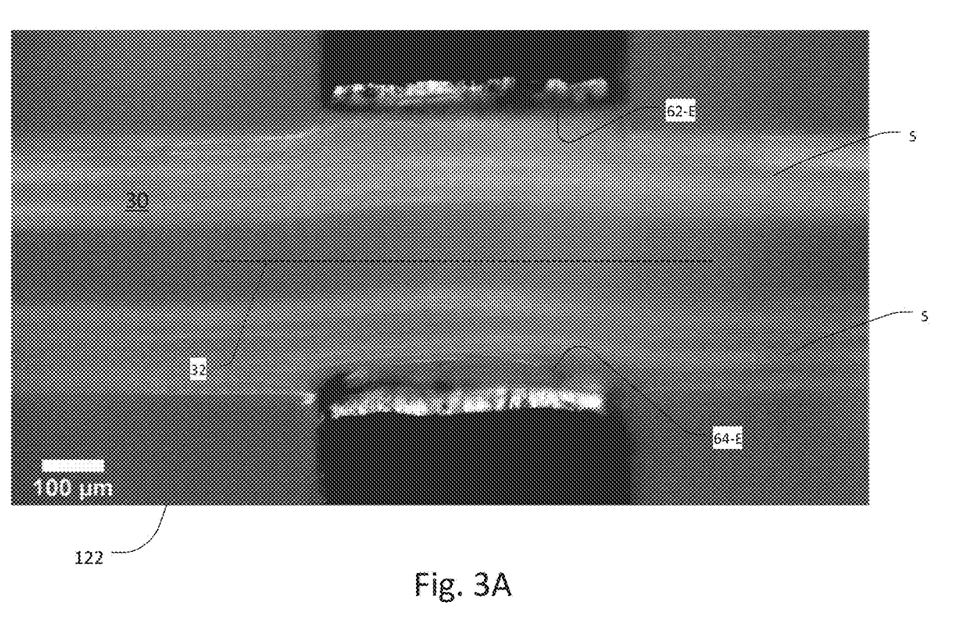
FIGS. 3A and 3B are images as would be captured by the image capture device for processing by the image analytics system.
Figure 3B:
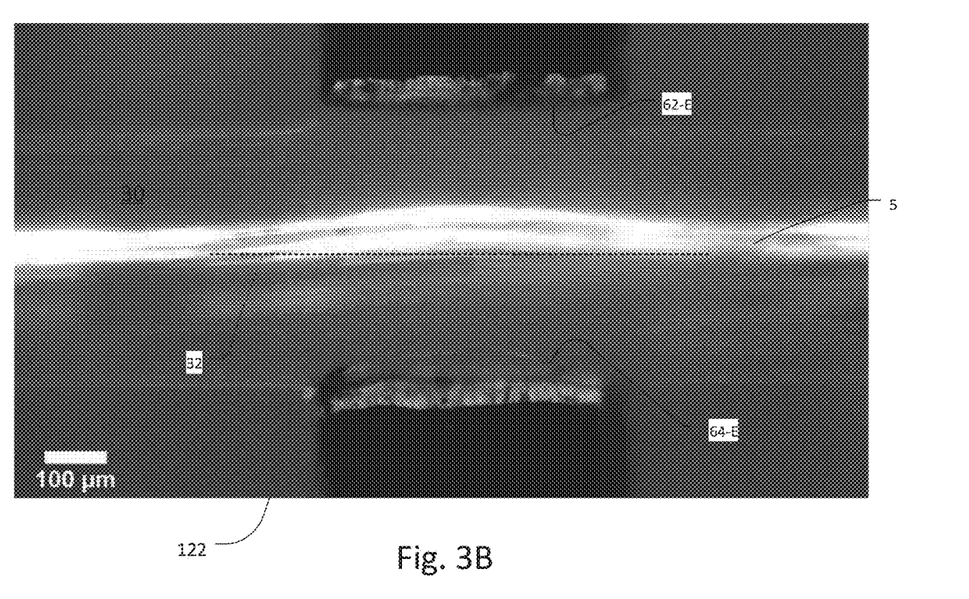

FIGS. 3A and 3B show exemplary images of the inter-electrode region 122 for different frequency and power settings of the ultrasonic driver module 116.

In one embodiment, the image analytics system 118 receives this image data from the microscope video image capture device 120 and executes an image analytics algorithm to identify the streams of cells 5 and their position(s) within the channel 30 and specifically relative to the centerline 32.

The image analytics system 118 provides the information concerning the location of the cells and the distribution of the streams of those cells to the controller 110. The controller then instructs the ultrasonic driver module 116 to change the frequency of the drive signal and also the amplitude of the drive signal that is applied to the acoustic transducer 60.

FIG. 3B is an image as would be captured by the image capture device 120 when the frequency and/or amplitude are tuned so that there is a single pressure node along the centerline 32 of the main channel 30. There is a single stream of cells 5, and the cells avoid contact with the ends 62-E, 64-E of the electroporation electrodes 62, 64.

Here, the image analytics system 118 receives this image data from the microscope video image capture device 120 and executes the image analytics algorithm to identify the single stream of cells 5 and its position within the channel 30 and specifically relative to the centerline 32.

The image analytics system 118 provides the information concerning the location of the cells and the distribution of the stream of those cells to the controller 110. In this case, the controller 110 will the maintain the current frequency and power setting for the ultrasonic driver module 116 since the stream of cells exhibit the proper centering.

Figure 4:
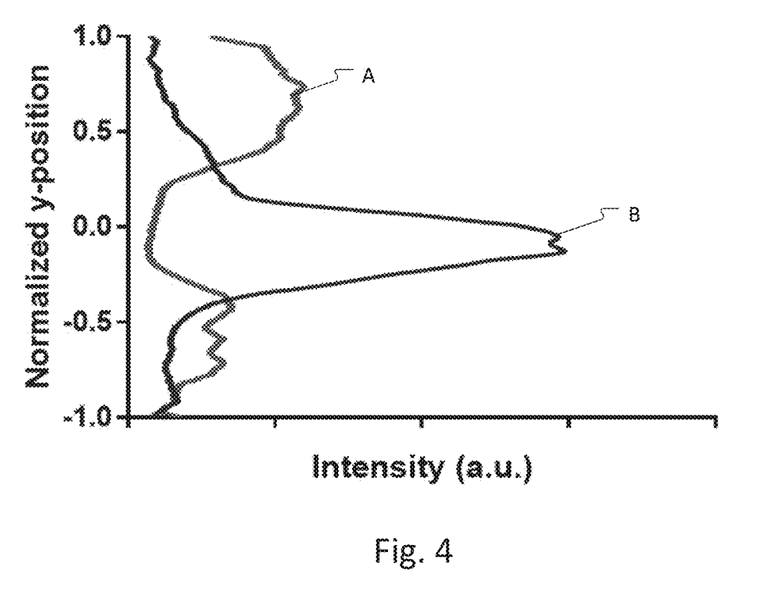
FIG. 4 illustrates plots showing y-axis distribution of the cells across the distance between the electrode ends 62-E, 64-E in the main channel 30 as would be produced by image analysis of the image analytics system.

FIG. 4 contains two plots A, B showing y-axis distributed of the cells, i.e., concentration of cells. These plots A, B would be produced by the image analytics system 118, in one example, based on analysis of the images from the microscope imaging system 112 and are provided to the controller 110. Based on this information, the controller 110 modulates the drive frequency and the amplitude of the drive signal generated by the ultrasonic driver module 116 so that the distribution of the cells approaches that of plot B.

Figure 5:
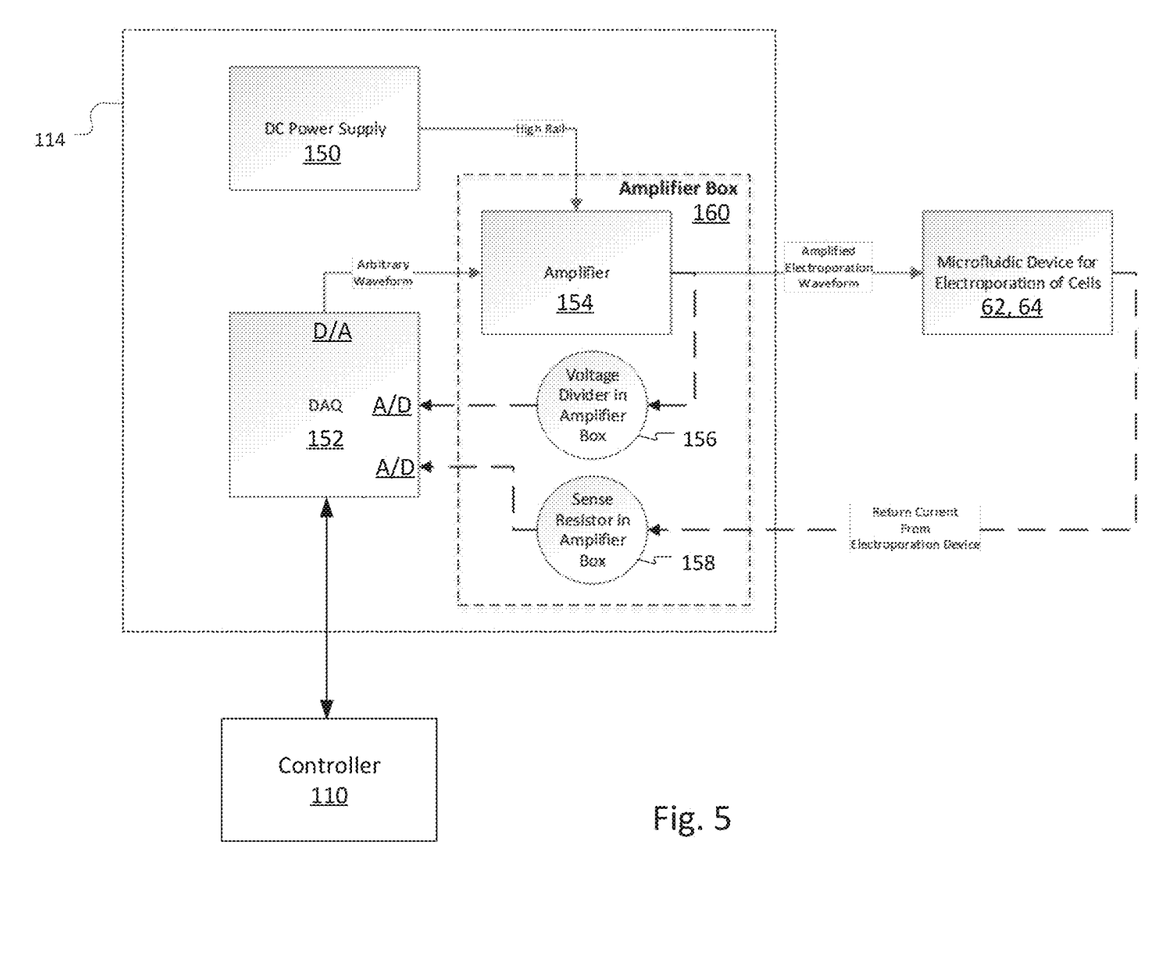
FIG. 5 is a block diagram showing one implementation of the electroporation driver module.

FIG. 5 is a block diagram showing one implementation of the electroporation driver module 114.

Data acquisition (DAQ) system 152 receives instructions from the controller 110 concerning the desired electroporation waveform, electroporation drive voltage, and electroporation current. The DAQ system 152 is preferably a microcontroller that includes a digital to analog converter port that generates the desired waveform as a time series of voltages. In this way, it functions as an arbitrary waveform generator.

The TTL signal generated by the DAQ 152 is provided to an amplifier 154 that generates the amplified electroporation waveform that is applied across the electroporation electrodes 62, 64 at the voltage levels specified by the controller 110. The amplifier 154 receives power from the DC power supply 150.

The DAQ 152 also includes two analog-to-digital conversion ports. These are used to monitor and provide feedback control to maintain the desired drive voltage and current specified by the commands issued from the controller 110. Specifically, a voltage divider 156 scales the voltage to a range required by the first analog-to-digital port of the DAQ 152. The first analog-to-digital port samples the stepped-down voltage level of the amplified electroporation waveform provided to the electrodes 62, 64. A sense resistor in the ground path of the second electroporation electrode 64 provides a voltage that is indicative of the electroporation current. This is sampled by the second analog-to-digital port of the DAQ 152.

FIGS. 6A through 6D are current measurements made using the sense resistor 158 in milliAmperes (mA) as a function of time plots in milliseconds (ms) showing different electroporation drive currents specified by the controller 110 and applied by the electroporation driver module 114.

Figure 6A:
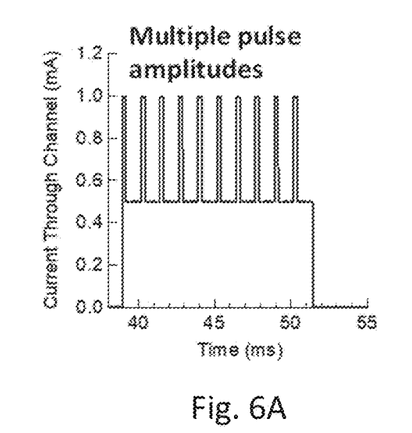
FIGS. 6A through 6D are plots of the different electroporation drive current waveforms in milliAmperes (mA) as a function of time in milliseconds (ms); the electroporation driver module can simultaneously measure the actual current delivered to cells in the electroporation channel, and examples of this are shown here.

FIG. 6A shows a multiple pulse amplitude drive current that maintains a minimal current level of about 0.45 mA with spikes up to 1 mA over each repeating 12 ms time range.

Figure 6B:
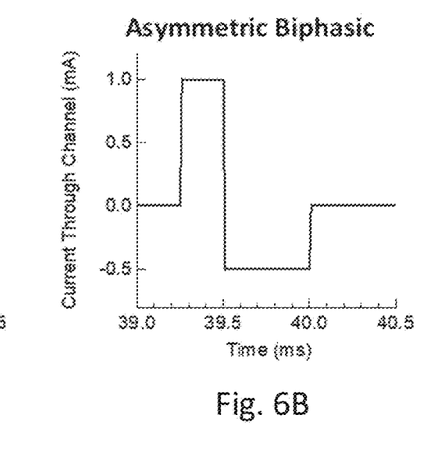

FIG. 6B shows in asymmetric biphasic drive signal that ranges between 1 mA and −0.5 mA over each approximately 1 ms cycle.

Figure 6C:
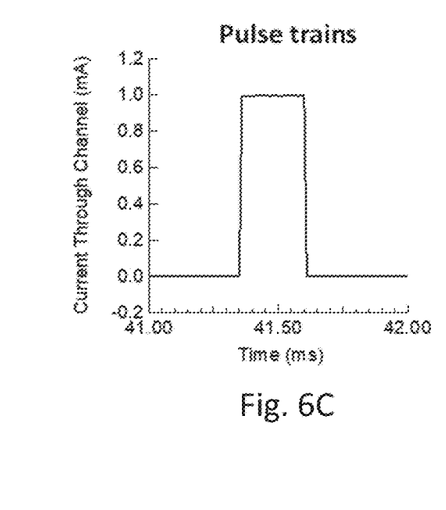

FIG. 6C shows a pulse train ranging from 0 mA to 1 mA with a pulse width of about 0.2 ms.

Figure 6D:
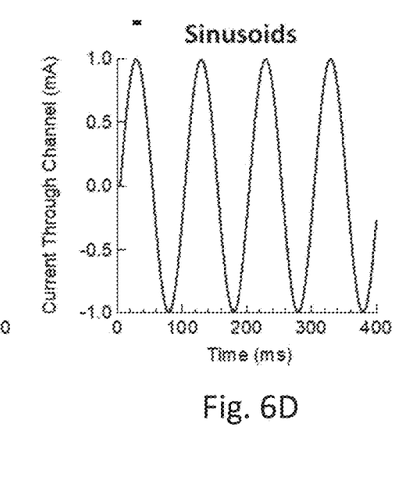

FIG. 6D shows a sinusoidal ranging between 1 mA and −1 mA with a period of about 100 ms.

Figure 7:
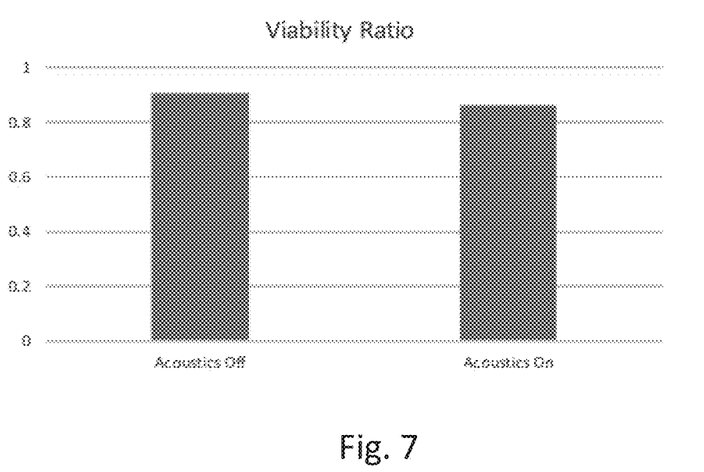
FIG. 7 is bar graph showing the viability of the cells passing through the device with and without acoustophoretic focusing.

FIG. 7 is a bar graph showing the changing viability of the cells passing through the device 10 with acoustics off and on. As shown, the operation of the acoustic transducer 60 has only a minor impact on cell viability.

Figure 8:
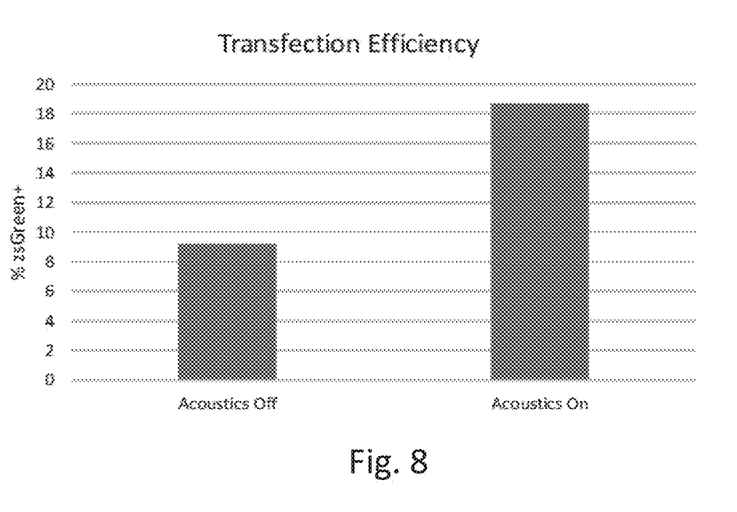
FIG. 8 is bar graph showing transfection efficiency of the cells passing through the device with and without acoustophoretic focusing.

FIG. 8 is a bar graph showing transfection efficiency of the cells passing through the device with acoustics off and on. As shown, the operation of the acoustic transducer 60 substantially improves the transfection efficiency from about 9% to over 18%.

While this invention has been particularly shown and described with references to preferred embodiments thereof, it will be understood by those skilled in the art that various changes in form and details may be made therein without departing from the scope of the invention encompassed. For example, in the future, multi-phase and/or sheath flows would be added in order to establish more control over cargo delivery. For example, the cell/cargo containing solution can be sheathed by an oil phase.

What is claimed is:

1. A method for introducing a payload into cells, the method comprising:
    flowing the cells between electroporation electrodes to facilitate delivery of the payload into the cells by flowing the cells through a microchannel system that has a main channel ending in a trifurcating outlet in which the cells are directed to a cell output channel that couples with a center of the main channel, and
    sensing the presence of cells by capturing images of the cells in the microchannel system and analyzing the images to determine locations of the cells, while acoustophoretically focusing the cells in a center of the main channel by modulating a drive signal in response to the analysis of the images.

2. The method of claim 1, wherein acoustophoretically focusing the cells comprises driving an acoustic transducer that is attached to a substrate holding the electroporation electrodes.

3. The method of claim 1, further comprising flowing spent cargo/solution downstream of the electroporation electrodes into two or more channels.

4. The method of claim 1, further comprising driving the electroporation electrodes with an arbitrary waveform generator.

5. The method of claim 1, wherein the presence of the cells is detected upstream of the electroporation electrodes.

6. The method of claim 1, further comprising energizing the electroporation electrodes in response to sensing the presence of cells.

7. The method of claim 1, further comprising measuring a current flow between the electroporation electrodes.

8. The method of claim 1, further comprising flowing the cells in the microchannel system that includes a substrate having the main channel ending in the trifurcating outlet.

9. The method of claim 8, further comprising acoustophoretically focusing the cells with an acoustic transducer that is attached to the substrate.

10. The method of claim 8, wherein the microchannel system has two or more channels of the outlet for receiving spent cargo/solution downstream of the electroporation electrodes.

11. The method of claim 1, further comprising analyzing the images to determine the locations of the cells in an inter-electrode region between the electroporation electrodes.

12. The method of claim 1, further comprising the microchannel system establishing a sheath flow of a cell incubation fluid on either side of an electroporation fluid between the electroporation electrodes.

\* \* \* \* \*